United States Patent [19]

Zeck

[11] 4,104,376

[45] Aug. 1, 1978

[54] SYNERGISTIC COMPOSITION FOR THE CONTROL OF INSECTS

[75] Inventor: Walter Maria Zeck, Vero Beach, Fla.

[73] Assignee: Mobay Chemical Corporation, Pittsburgh, Pa.

[21] Appl. No.: 813,722

[22] Filed: Jul. 7, 1977

[51] Int. Cl.² .......................... A01N 9/02; A01N 9/20; A01N 9/36
[52] U.S. Cl. .................................... 424/216; 424/326
[58] Field of Search ................................ 424/216, 326

[56] References Cited

U.S. PATENT DOCUMENTS

| | | | |
|---|---|---|---|
| 3,825,636 | 7/1974 | Kishino et al. | 260/964 |
| 3,864,497 | 2/1975 | Harrison et al. | 424/326 |

*Primary Examiner*—Allen J. Robinson
*Attorney, Agent, or Firm*—Burgess, Dinklage & Sprung

[57] ABSTRACT

Insecticidal compositions in the form of synergistic combinations of O-ethyl-O-[4-(methylthio)phenyl-S-propyl] phosphorodithioate and N-methyl-N'-2,4-xylyl-N-(N-2,4-xylyl-formimidoyl) formamidine which are individually known compounds, which combinations possess synergistic insecticidal properties especially for the control of insects which infest cotton.

9 Claims, No Drawings

SYNERGISTIC COMPOSITION FOR THE CONTROL OF INSECTS

The present invention relates to and has for its objects the provision of particular new insecticidal compositions in the form of synergistic combinations of O-ethyl-O-[4-(methylthio)phenyl]-S-propyl phosphorodithioate (Compound A) and N-methyl-N'-2,4-xylyl-N-(N-2,4-xylyl-formimidoyl) formamidine (Compound B) which are individually known compounds which combinations possess outstanding synergistic insecticidal properties especially for growing cotton optionally in the form of carrier composition mixtures of such synergistic combinations with solid and/or liquid dispersible carrier vehicles, and methods for using such synergistic combinations in a new way especially for combating insects, with other and further objects becoming apparent from a study of the within specification and accompanying examples.

It is taught in U.S. Pat. No. 3,825,636 that compounds such as O-ethyl-O-[4-(methylthio)phenyl]-S-propyl phosphorodithioate can be used as insecticides.

It is also known from that N-methyl-N'-2,4-xylyl-N-(N-2,4-xylyl-formimidoyl)formamidine is suitable for combating insects.

It has now been found that combinations of these wherein the O-ethyl-O-[4-(methylthio)phenyl]-S-propyl phosphorodithioate is present in a weight ratio relative to the N-methyl-N'-2,4-xylyl-N-(N-2,4-xylyl-formimidoyl)formamidine of 1 to about 0.1–1 and preferably 1 to about 0.2–0.5 is especially effective in fighting insects and particularly *Lepidoptera,* especially *Heliothis* species, which infest crops such as corn, soybeans, tobacco and particularly cotton.

Surprisingly, the insecticidal effectiveness of the particular new synergistic combinations of active compounds according to the present invention is substantially higher than the sum of the separate effects of the individual active compounds. This is not merely a supplementary or additive effect, but rather a genuine synergistic effect which was not to be foreseen. Significantly, this synergistic effect is particularly great when limited to specific ratios of concentration as noted above.

Advantageously, the synergistic combinations of active compounds according to the present invention are markedly superior to known active compounds conventionally used for insect control in agricultural crops. The instant synergistic combinations of active compound therefore represent a valuable contribution to the art of insect control agents.

The compositions can be applied to a variety of insects, both of the biting and sucking type.

To the sucking insects there belong, in the main, aphids (*Aphididae*) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (*Thysanoptera*), such as *Hercinothrips femoralis,* bugs, for example the beet bug (*Piesma quadrata*), the red cotton bug (*Dysdercus intermedius*), the bed bug (*Cimex lectularius*), the assassin bug (*Rhodnius prolixus*) and Chagas' bug (*Triatoma infestans*) and, further, cicadas, such as *Euscelis bilobatus* and *Nephotettix bipunctatus.*

In the case of the biting insects, above all there should be mentioned butterfly caterpillars (*Lepidoptera*) such as the diamond-back moth (*Plutella maculipennis*), the gypsy moth (*Lymantria dispar*), the brown-tail moth (*Euproctis chrysorrhoea*) and tent caterpillar (*Malacosoma neustria*); further, the cabbage moth (*Namestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia Kühniella*) and greater wax moth (*Galleria mellonella*), the cotton bollworm (*Heliothis zea*), and the tobacco budworm (*Heliothis virescens*).

Also to be classed with the biting insects are beetles (*Coleoptera*), for example the granary weevil (*Sitophilus granarius = Calandra granaris*), the Colorado beetle (*Leptinotarsa decemlineata*), the dock beetle (*Gastrophysa viridula*), the mustard beetle (*Phaedon cochleariae*), the blossom beetle (*Meligethes aeneus*), the boll weevil (*Authonomus grandis*), the raspberrry beetle (*Buturus tomentosus*), the bean weevil (*Bruchidius = Acanthoscelides obtectus*), the leather beetle (*Dermestes frischi*), the khapra beetle (*Trogoderma granarium*), the flour beetle (*Tribolium castaneum*), the northern corn billbug (*Calandra* or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example, wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (*Leucophaea* or *Rhyoaribya maderae*), oriental cockroach (*Blatta orientalis*), the giant cockroach (*Blaberus giganteus*) and the black giant cockroach (Blaberus fuscus) as well as *Henschoutedenia flexivitta;* further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further gnats, for example mosquitoes such as the yellow fever mosquito (*Aëdes aegypti*), the northern house mosquito (*Culex pipens*) and the malaria mosquito (*Anopheles stephensi*).

Of these, the invention is especially valuable for use against Lepidoptera and especially of the sub-genus Heliothis, e.g. the cotton boll worm complex (*Heliothis virescens* and *Heliothis zea*) and the fall army worm (*Spodoptera frugiperda*). In addition to application to cotton, the composition is also suited for application to corn, soybeans and tobacco.

The active compounds according to the instant invention can be utilized, if desired, in the form of the usual formulations or compositions with conventional inert (i.e. plant compatible or herbicidally inert) pesticide diluents or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g. benzene, toluene, xylene, alkyl naphthalenes, etc.), halogenated especially chlorinated, aromatic hydrocarbons (e.g. chloro-benzenes, etc.), cycloalkanes, (e.g. cyclohexane, etc.). paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide etc.) sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc. and especially alkyl arylpolyglycol ethers, magnesium stearate, sodium oleate, etc.); and/or dispersing agents such as lignin, sulfite waste liquors, methyl cellulose, etc.

Such active compounds may be employed alone or in the form of mixtures with such solid and/or liquid dispersible carrier vehicles and/or other known compatible active agents, especially plant protection agents, such as other insecticides, or acaricides, nematocides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compounds are present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contempaltes over-all compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compounds or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed. In this process it is possible to use highly concentrated liquid compositions with said liquid carrier vehicles containing from about 20 to 95% by weight of the active compounds or even the 100% active substances alone, e.g. about 20–100% by weight of the active compounds.

The mixture of active materials is usually applied in such amount as to provide about 0.2 to 2 and preferably about 0.5 to 1.5 pounds of active materials per acre.

Furthermore, the present invention contemplates methods of selectively killing, combating or controlling pests, which comprises applying to at least one of correspondingly (a) such pests and (b) the corresponding habitat thereof, i.e. the locus to be protected, e.g. to a growing crop, to an area where a crop is to be grown or to a domestic animal, a correspondingly combative or toxic amount, i.e. a pesticidally effective amount, of the particular active compounds of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compounds utilized in admixture with the carrier vehicle will depend upon the intended application. Therefore, in special cases it is possible to go above or below the aforementioned concentration ranges.

The unexpected superiority and outstanding activity of the particular compositions of the present invention are illustrated, without limitation, by the following examples:

SYNERGISM IN OVICIDAL ACTIVITY

Example 1

*Heliothis virescens*

To produce a suitable preparation of active material, O-ethyl-O-[4-(methylthio)phenyl]-S-propyl phosphorodithioate (A) is dissolved in xylene to form a concentrate of 6 pounds per gallon. N-methyl-N'-2,4-xylyl-N-(N-2,4-xylyl-formimidoyl) formamidine (B) is dissolved in xylene to form a concentrate of 1.5 pounds per gallon. The requisite amounts of concentrates are combined to give the desired proportions of active materials and the combined concentrates are diluted with water to the desired overall concentrations.

Cotton plants, growing in small peat pots, in the two true leaf stage, are placed in an oviposition container, holding 4 plants. 4 Gravid female moths of *Heliothis virescens*, about 6 days old, are introduced and maintained in the container overnight for a period of 16 hours. They are fed on a 5% sugar solution, absorbed on a cotton pad. After this period, the plants are inspected, and only those plants are used for the trial which have at least 20 but no more than 40 eggs deposited on the surface of the two true leaves. All other eggs on the plant or the pot are removed with a vacuum needle, so that all remaining eggs are exposed to the later spray application from the top.

24 Hours after the initial introduction of the moths, plants and eggs are sprayed with the test solutions, using a conveyor belt which moves the plants at a constant speed under nozzles spraying them from the top at a constant pressure of 28 psi, delivering a predetermined amount of chemical in 20 gallons of total liquid per acre. There is little coverage on the lower surface of the leaf, and no drip off. Three plants are sprayed per treatment. Each treated plant is placed in a 1 gallon cardboard container. The top edge of the container is covered with Vaseline petroleum jelly to prevent escape of the hatching larvae. Eggs start hatching 3 days after spraying.

2 Days after the beginning of the hatching, evaluations are made under a microscope on the percent of egg hatch, kill and larvae survival. The results are set forth in Table 1.

Table 1

| Run | A (Active Compound Conc. %) | B→ 0 | 0.003 | % Ovicidal Activity 0.01 | 0.03 | 0.1 |
|---|---|---|---|---|---|---|
| 1 | 0 | | 11 | 18 | 29 | 54 | 59 |
| 2 | 0.01 | | 11 | 11 | 67 | 79 | |
| 3 | 0.03 | | 17 | 21 | 74 | | |
| 4 | 0.1 | | 3 | 82 | 96 | 100 | |

Those results underscored in the table show clearly synergistic action. This can be seen by the fact that each underscored number is far more than the sum of the activities for each of the compounds alone at the indicated concentration. For example, A at 0.1% concentration produces 3% kill and B at 0.003% concentration produces 18% kill. When combined it would be expected the kill would be about 3 + 18 = 21% but it actually is 82%.

Example 2

*Heliothis virescens*

The procedure of Example 1 is re-run and the results obtained are set forth in Table 2.

Table 2

| Run | A (Active Compound Conc. %) | B→ 0 | 0.003 | % Ovicidal Activity 0.01 | 0.03 | 0.1 |
|---|---|---|---|---|---|---|
| 5 | 0 | | 0 | 8 | 54 | 30 | 49 |
| 6 | 0.01 | | 6 | 9 | 52 | 65 | |
| 7 | 0.03 | | 0 | 59 | 76 | 96 | |
| 8 | 0.1 | | 12 | 95 | 85 | 98 | |

Example 3

The procedure of Example 1 is repeated except that the ova are from *Heliothis zea*. The results obtained are set forth in Table 3.

Table 3

| Run | A (Active Compound Conc. %) | B→ 0 | 0.003 | % Ovicidal Activity 0.01 | 0.03 | 0.1 |
|---|---|---|---|---|---|---|
| 9 | 0 | | 0 | 3 | 31 | 9 | 62 |
| 10 | 0.003 | | 0 | 29 | 18 | 25 | |
| 11 | 0.01 | | 15 | 25 | 7 | 75 | |
| 12 | 0.03 | | 27 | 24 | 17 | 80 | |
| 13 | 0.1 | | 64 | — | 100 | — | |

SYNERGISM IN LARVICIDAL ACTIVITY

Example 4

In this example solutions are prepared and plants sprayed as in Example 1 except there is no prior exposure of the plants to insects to result in deposit of ova. Instead, after spraying and drying, $L_3$ stage larvae of *Heliothis virescens* are caged on the plants, 4 cages with 5 larvae each, with evaluation for mortality after 48 hours. The results obtained are set forth in Table 4.

Table 4

| Run | A (Active Compound Conc. %) | B→ 0 | % Larvicidal Activity ($L_3$) 0.01 | 0.03 | 0.1 |
|---|---|---|---|---|---|
| 14 | 0 | | 0 | 0 | 21 | 0 |
| 15 | 0.01 | | 0 | 14 | 14 | 14 |
| 16 | 0.03 | | 21 | 36 | 57 | 71 |
| 17 | 0.1 | | 86 | 93 | 93 | 93 |

The underscored results show synergy. When (A) alone is used in such concentration that it almost produces 100% kill, it masks the synergy since there is little left for (B) to do.

Example 5

The test method of Example 1 is twice more re-run evaluating the survival of the hatched $L_1$ of larvae of *Heliothis virescens* at various concentrations of active materials. Results are shown in Tables 5 and 6 where the underlined results show synergy; at highest levels of (A) synergy is masked.

Table 5

| Run | A (Active Compound Conc. %) | B→ 0 | 0.003 | % Larvicidal Activity ($L_1$) 0.01 | 0.03 | 0.1 |
|---|---|---|---|---|---|---|
| 18 | 0 | | 0 | 4 | 0 | 20 | 8 |
| 19 | 0.003 | | 16 | 12 | 55 | 64 | |
| 20 | 0.01 | | 88 | 88 | 100 | 100 | |
| 21 | 0.03 | | 100 | 100 | 100 | 100 | |

Table 6

| Run | A (Active Compound Conc. %) | B→ 0 | 0.003 | % Larvicidal Activity ($L_1$) 0.01 | 0.03 | 0.1 |
|---|---|---|---|---|---|---|
| 22 | 0 | | 0 | 0 | 4 | 15 | 34 |
| 23 | 0.003 | | 11 | 21 | 100 | 100 | |
| 24 | 0.01 | | 100 | 92 | 100 | 100 | |

It will be appreciated that the instant specification and examples are set forth by way of illustration and not limitation, and that various modifications and changes may be made without departing from the spirit and scope of the present invention.

What is claimed is:

1. A synergistic insecticidal composition comprising an insecticidally effective amount of O-ethyl-O-[4-(methylthio)-phenyl]-S-propyl phosphorodithioate and N-methyl-N'-2,4-xylyl-N-(N-2,4-xylyl-formimidoyl) formamidine in a weight ratio of about 1:0.03–10.

2. A composition according to claim 1 wherein the weight ratio is about 1:0.2–0.5.

3. A method for combating insects which comprises applying to such insects or an insect habitat an insecticidally effective amount of a composition comprising O-ethyl-O-[4-(methylthio)-phenyl]-S-propyl phosphorodithioate and N-methyl-N'-2,4-xylyl-N-(N-2,4-xylyl-formimidoyl) formamidine in a weight ratio of about 1:0.03–10.

4. The method according to claim 3, wherein the weight ratio is about 1:0.2–0.5.

5. The method according to claim 3, wherein the composition is applied to a field in which cotton, corn, soybeans or tobacco is grown.

6. The method according to claim 3, wherein the composition is applied to a field in which cotton is grown.

7. The method according to claim 3, wherein the insect combated is of the order *Lepidoptera*.

8. The method according to claim 7, wherein the insect combated is of the genus *Heliothis*.

9. The method according to claim 8, wherein the composition is applied to a field in which cotton is grown, and the ingredients are present in a weight ratio of about 1:0.2–0.5.

* * * * *